(12) United States Patent
Bachmann et al.

(10) Patent No.: US 10,689,325 B2
(45) Date of Patent: Jun. 23, 2020

(54) PROCESS FOR THE PREPARATION OF AN ANTIBODY-RIFAMYCIN CONJUGATE

(71) Applicant: Genentech, Inc., South San Francisco, CA (US)

(72) Inventors: Stephan Bachmann, Roethenbach (CH); Serena Maria Fantasia, Saint-Louis (FR); Michael Jansen, Bartenheim (FR); Stefan Koenig, San Francisco, CA (US); Xin Linghu, Burlingame, CA (US); Sebastian Rieth, Bad Saeckingen (DE); Nathaniel L. Segraves, Sunnyvale, CA (US); Andreas Zogg, Frenkendorf (CH)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/415,612

(22) Filed: May 17, 2019

(65) Prior Publication Data
US 2019/0270695 A1    Sep. 5, 2019

Related U.S. Application Data

(62) Division of application No. 15/448,894, filed on Mar. 3, 2017, now Pat. No. 10,336,683.

(60) Provisional application No. 62/303,556, filed on Mar. 4, 2016.

(51) Int. Cl.

| C07D 498/22 | (2006.01) |
|---|---|
| C07C 213/00 | (2006.01) |
| C07C 201/12 | (2006.01) |
| C07C 213/02 | (2006.01) |
| C07K 16/12 | (2006.01) |
| C07D 498/04 | (2006.01) |
| A61K 47/68 | (2017.01) |
| C07D 498/18 | (2006.01) |
| A61K 39/00 | (2006.01) |

(52) U.S. Cl.
CPC ........ *C07C 213/00* (2013.01); *A61K 47/6803* (2017.08); *A61K 47/6835* (2017.08); *C07C 201/12* (2013.01); *C07C 213/02* (2013.01); *C07D 498/04* (2013.01); *C07D 498/18* (2013.01); *C07K 16/1267* (2013.01); *C07K 16/1271* (2013.01); *A61K 2039/505* (2013.01); *C07K 2317/77* (2013.01)

(58) Field of Classification Search
CPC .................................................. C07D 498/22
See application file for complete search history.

(56) References Cited

U.S. PATENT DOCUMENTS

| 3,150,046 A | 9/1964 | Sensi et al. |
|---|---|---|
| 4,690,919 A | 9/1987 | Yamane et al. |
| 4,983,602 A | 1/1991 | Yamane et al. |
| 6,322,788 B1 | 11/2001 | Kim |
| 7,265,107 B2 | 9/2007 | Li et al. |
| 7,271,165 B2 | 9/2007 | Van Duzer et al. |
| 7,342,011 B2 | 3/2008 | Van Duzer et al. |
| 7,498,298 B2 | 3/2009 | Doronina et al. |
| 7,521,541 B2 | 4/2009 | Eigenbrot et al. |
| 7,547,692 B2 | 6/2009 | Van Duzer et al. |
| 7,678,791 B2 | 3/2010 | Ding et al. |
| 7,723,485 B2 | 5/2010 | Junutula et al. |
| 7,884,099 B2 | 2/2011 | Ding et al. |
| 8,524,691 B2 | 9/2013 | Dietrich et al. |
| 2014/0356375 A1 | 12/2014 | Brown et al. |
| 2015/0147328 A1 | 5/2015 | Lee et al. |
| 2016/0024190 A1 | 1/2016 | Ohsawa et al. |
| 2017/0252457 A1 | 9/2017 | Bachmann et al. |

FOREIGN PATENT DOCUMENTS

| WO | 2009052249 A1 | 4/2009 |
|---|---|---|
| WO | 2014193722 A1 | 12/2014 |
| WO | 2014194247 A1 | 12/2014 |

OTHER PUBLICATIONS

Carl, et al., "A novel connector linkage applicable in prodrug design", J Med Chem 24(5), 479-480 (1981).
Doronina, et al., "Development of potent monoclonal antibody auristatin conjugates for cancer therapy", Nat Biotechnol 21, 778-784 (2003).
Doronina, et al., "Novel Peptide Linkers for Highly Potent Antibody—Auristatin Conjugate", Bioconjugate Chem 19, 1960-1963 (2008).
(Continued)

*Primary Examiner* — Bruck Kifle
(74) *Attorney, Agent, or Firm* — Viksnins Harris Padys Malen LLP

(57) ABSTRACT

Processes are described for the preparation of F-benzoxazinorifamycin I:

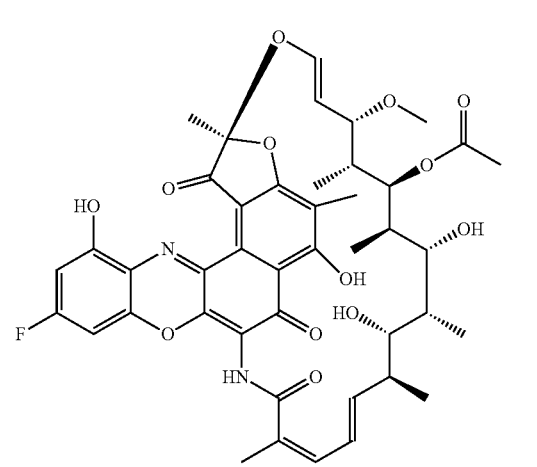

and intermediates for conjugation with an antibody.

8 Claims, 1 Drawing Sheet

(56) References Cited

OTHER PUBLICATIONS

Dubowchik, et al., "Cathepsin B-Labile Dipeptide Linkers for Lysosomal Release of Doxorubicin from Internalizing Immunoconjugates: Model Studies of Enzymatic Drug Release and Antigen-Specific in Vitro Anticancer Activity", Bioconjugate Chem 13, 855-869 (2002).
Dubowchik, et al., "Cathepsin B-Sensitive Dipeptide Prodrugs. 1. A Model Study of Structural Requirements for Efficient Release of Doxorubicin", Bioorganic & Medicinal Chemistry Letters 8, 3341-3346 (1998).
Dubowchik, et al., "Doxorubicin Immunoconjugates Containing Bivalent, Lysosomally-Cleavable Dipeptide Linkages", Bioorganic & Medicinal Chemistry Letters 12, 1529-1532 (2002).
Flygare, et al., "Antibody-Drug Conjugates for the Treatment of Cancer", Chem Biol Drug Des 81, 113-121 (2013).
Fujii, et al., "In Vitro and In Vivo Antibacterial Activities of KRM-1648 and KRM-01657, New Rifamycin Derivatives", Antimicrobial Agents and Chemotherapy 38(5), 1118-1122 (1994).
Junutula, et al., "Rapid identification of reactive cysteine residues for site-specific labeling of antibody-Fabs", Journal of Immunological Methods 332, 41-52 (2008).
Junutula, et al., "Site-specific conjugation of a cytotoxic drug to an antibody improves the therapeutic index", Nature Biotechnology 26(8), 925-932 (2008).
Kaizer, et al., "TEMPO-initiated oxidation of 2-aminophenol to 2-aminophenoxazin-3-one", Journal of Molecular Catalysis A: Chemical 180, 91-96 (2002).
Kump, et al., "To the Knowledge of Rifamycin-S. Reactions of the quinoid nucleus", Modifications by Antibiotics, 9th Part [1], 2348 Helvetica Chimica Acta 56(7), No. 244, 72 pages, including English Summary (1973).
Lantto, et al., "Capturing the Natural Diversity of the Human antibody Response against Vaccinia Virus", Journal of Virology 85(4), 1820-1833 (2011).
Lehar, et al., "Novel antibody-antibiotic conjugate eliminates intracellular S. aureus", Nature 527(7578), 323-328 (2015).
Linghu, et al., "Highly Efficient Synthesis of a *Staphylococcus aureus* Targeting Payload to Enable the First Antibody—Antibiotic Conjugate", Chem Eur J 24, 2837-2840 (2018).
Rothstein, et al., "Development potential of rifalazil", Expert Opinion Investig Drugs 12(2), 255-271 (2003).
Rothstein, et al., "Development potential of rifalazil and other benzoxazinorifamycins", Expert Opinion Investig Drugs 15(6), 603-623 (2006).
Shen, et al., "Conjugation site modulates the in vivo stability and therapeutic activity of antibody-drug conjugates", Nature Biotech 30(2), 184-191 (2012).
Staben, et al., "Targeted drug delivery through the traceless release of tertiary and heteroaryl amines from antibody-drug conjugates", Nature Chemistry 8, 1112-1119 (2016).
Yamane, et al., "Synthesis and Biological Activity of 3'-Hydroxy-5'-aminobenzoxazinorifamycin Derivatives", Chem Pharm Bull 41(1), 148-155 (1993).
Yamane, et al., "Synthesis and Biological Activity of 5'-Aminobenzoxazinorifamycin Derivatives", Chem Pharm Bull 40(10), 2707-2711 (1992).
Zhou et al., "Pharmacokinetics and pharmacodynamics of DSTA4637A: A novel THIOMAB™ antibody antibiotic conjugate against *Staphylococcus aureus* in mice", MABS 8(8), 1612-1619 (2016).

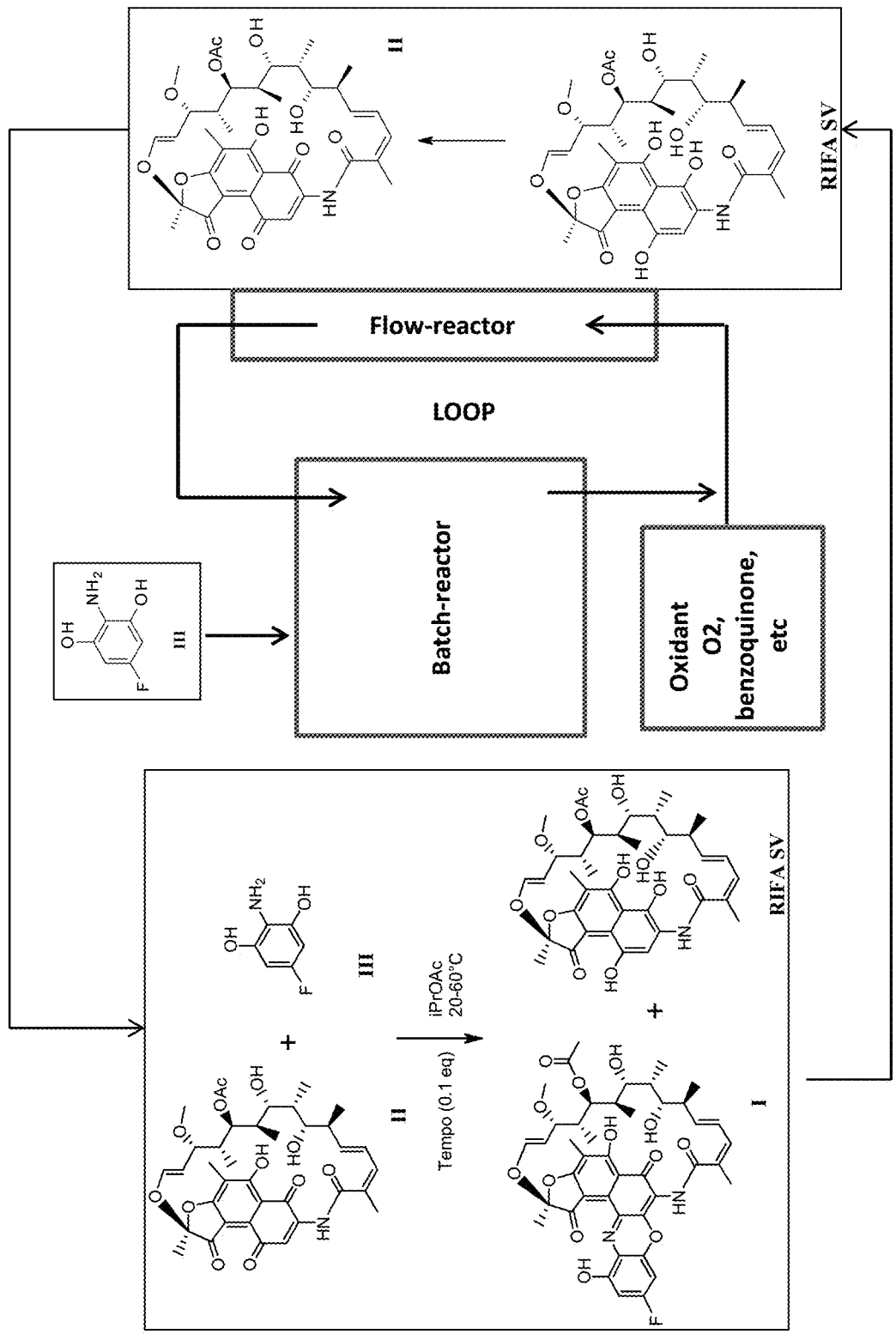

PROCESS FOR THE PREPARATION OF AN ANTIBODY-RIFAMYCIN CONJUGATE

CROSS REFERENCE TO RELATED APPLICATIONS

This divisional application claims priority to U.S. application Ser. No. 15/448,894, filed 3 Mar. 2017, which is a non-provisional application and claims priority to U.S. Provisional Application Ser. No. 62/303,556 filed on 4 Mar. 2016, the contents of which are incorporated by reference in their entirety.

FIELD OF THE INVENTION

The invention relates to methods of making an antibody-rifamycin conjugate compound.

BACKGROUND OF THE INVENTION

Antibody-drug conjugates (ADC), also known as immunoconjugates, are targeted chemotherapeutic molecules which combine ideal properties of both antibodies and cytotoxic drugs by targeting potent cytotoxic drugs to antigen-expressing tumor cells (Teicher, B. A. (2009) Curr. Cancer Drug Targets 9:982-1004), thereby enhancing the therapeutic index by maximizing efficacy and minimizing off-target toxicity (Carter, P. J. and Senter P. D. (2008) The Cancer Jour. 14(3):154-169; Chari, R. V. (2008) Acc. Chem. Res. 41:98-107. ADC comprise a targeting antibody covalently attached through a linker unit to a cytotoxic drug moiety. Immunoconjugates allow for the targeted delivery of a drug moiety to a tumor, and intracellular accumulation therein, where systemic administration of unconjugated drugs may result in unacceptable levels of toxicity to normal cells as well as the tumor cells sought to be eliminated (Polakis P. (2005) Curr. Opin. Pharmacol. 5:382-387).

The concept of ADC in cancer therapy has been expanded into antibacterial therapy, where the drug portion is an antibiotic, resulting in antibody-antibiotic conjugate (AAC). An anti-WTA monoclonal antibody was conjugated by a covalent linker attachment to one or more rifamycin-type antibiotic moieties (Lehar, S. et al (2015) "Novel antibody-antibiotic conjugate eliminates intracellular *S. aureus*" Nature 527(7578) 323-328; Staben, L. R., et al (2016) "Targeted drug delivery through the traceless release of tertiary and heteroaryl amines from antibody-drug conjugates" Nature Chemistry 8 (12):1112-1119; Zhou, C., et al (2016) "Pharmacokinetics and pharmacodynamics of DSTA4637A: A novel THIOMAB™ antibody antibiotic conjugate against *Staphylococcus aureus* in mice" MABS 8 (8):1612-1619; WO 2014/194247), and other antibiotics (WO 2014/193722). It was demonstrated that intracellular reservoirs of *S. aureus* in mice comprise a virulent subset of bacteria that can establish infection even in the presence of vancomycin. The anti-WTA rifamycin conjugate is a novel therapeutic that effectively kills intracellular *S. aureus*. This antibody-antibiotic conjugate (AAC) consists of *S. aureus* targeting antibody conjugated to a highly efficacious antibiotic is activated only after it is released in the proteolytic environment of the phagolysosome. The antibody-antibiotic conjugate is superior to vancomycin for treatment of bacteremia and provides direct evidence that intracellular *S. aureus* represents an important component of invasive infections.

SUMMARY OF THE INVENTION

The invention relates to methods of making the antibody-rifamycin conjugate compound:

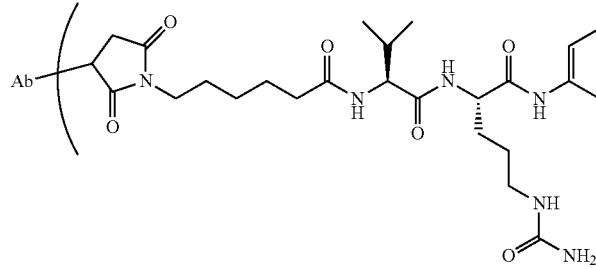
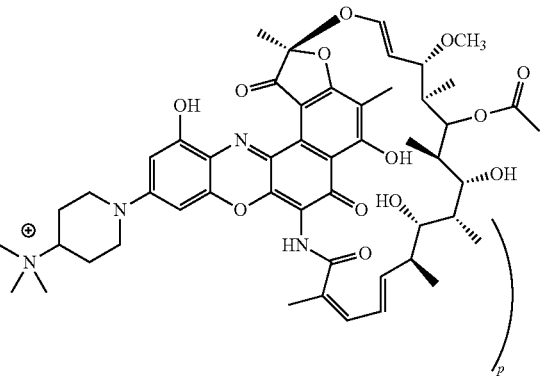

An aspect of the invention is a process for the preparation of F-benzoxazinorifamycin I,

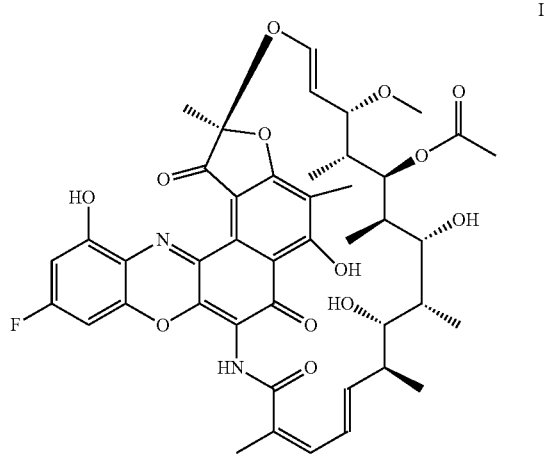 [SMILES: CO[C@H]1/C=C/O[C@@]2(C)Oc3c(C)c(O)c4c(=O)c(c5oc6cc(F)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

comprising reacting rifamycin S II, 2-amino-5-fluorobenzene-1,3-diol III, and an oxidant selected from TEMPO, benzoquinone, and copper salts, to form I

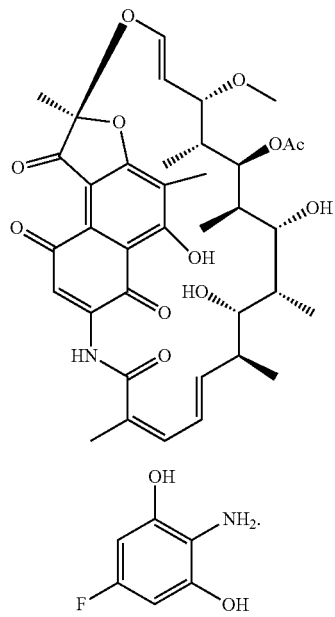

Another aspect of the invention is a process for the preparation of 2-amino-5-fluorobenzene-1,3-diol III, comprising:

(a) reacting 1,3,5-trifluoro-2-nitrobenzene VIII and benzyl alcohol, and a basic reagent selected from lithium bis(trimethylsilylamide), lithium diisopropylamide, and an alkoxide reagent, to form (((5-fluoro-2-nitro-1,3-phenylene)bis(oxy))bis(methylene))dibenzene IX

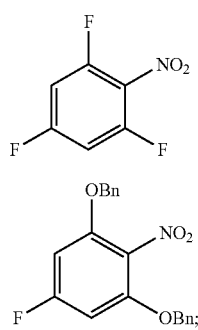

and (b) reacting IX with hydrogen gas and a heterogeneous metal catalyst to form III.

BRIEF DESCRIPTION OF THE DRAWINGS

FIG. 1 shows a schematic of the general process for oxidative cyclization of Rifamycin S II with 2-amino-5-fluorobenzene-1,3-diol III to give F-benzoxazinorifamycin I (Scheme 1) by a semi-continuous loop process with a flow-reactor and batch-reactor.

DEFINITIONS

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers (stereocenters), and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

Preparation of an Antibody-Rifamycin Conjugate

The present invention includes processes, methods, reagents, and intermediates for the synthesis of an antibody-rifamycin conjugate compound depicted as:

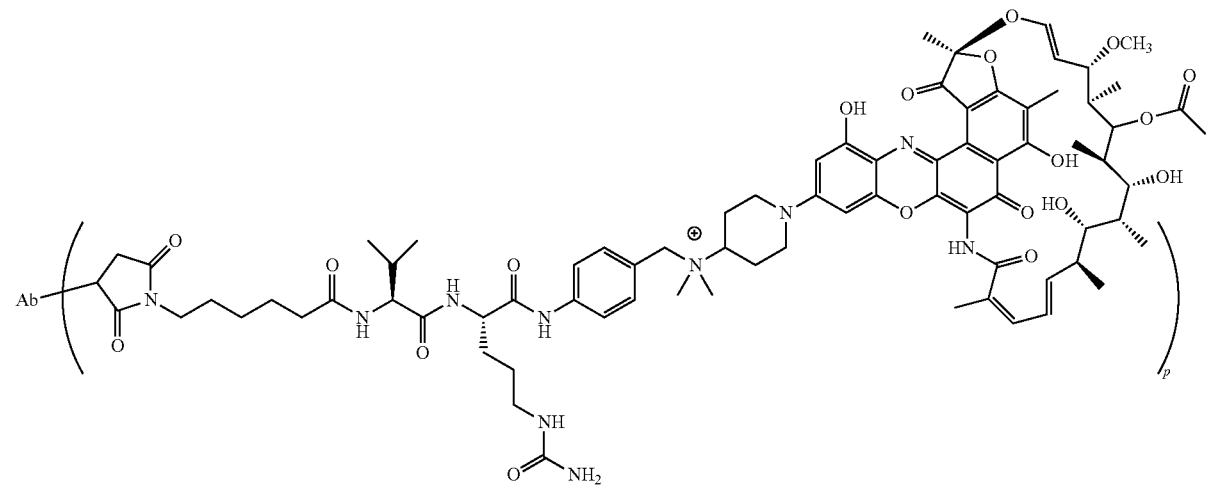

where Ab is an anti-WTA (wall teichoic acid) antibody and p is an integer from 1 to about 4 (Lehar, S. et al (2015) "Novel antibody-antibiotic conjugate eliminates intracellular S. aureus" 527(7578) 323-328; WO 2014/194247; WO 2014/193722, the contents of each of which are incorporated by reference). The antibody is covalently attached to the rifamycin antibiotic moiety through a linker comprising a dipeptide (valine-citrulline) and p-aminobenzyl spacer that is cleaved physiologically (Carl, P. L. et al (1981) J. Med. Chem. 24(5):479-480; Dubowchik, G. M. et al (1998) Chem. Lett. 8:3341-3346; Dubowchik, G. M. et al (2002) Bioconjugate Chem. 13:855-869). The tertiary amine terminus of the rifamycin moiety forms a quaternary ammonium salt in the antibody-rifamycin conjugate compound to release an active antibiotic when cleaved. The quaternary ammonium group may also serve to modulate cleavage, optimize solubility and minimize aggregation of the conjugate compound.

The thick peptidoglycan layers of Gram-positive bacteria are connected to pathogen-specific polyanionic glycopolymers called wall-teichoic acids (WTA). Specifically, S. aureus produces WTA composed of phospho-ribitol repeating units that are further modified by either α(alpha)- or β(beta)-O-linked N-acetylglucosamine (GlcNAc) sugar modifications mediated by TarM or TarS glycosyltransferases, respectively (Winstel, V., et al (2014) Int J Med Microbiol 304, 215-221). Teichoic acids (TA) are bacterial polysaccharides found within the cell wall of Gram-positive bacteria including SA. Wall teichoic acids (WTA) are those covalently linked to the peptidoglycan (PDG) layer of the cell wall; whereas lipoteichoic acids (LTA) are those covalently linked to the lipids of the cytoplasmic membrane (Xia et al. (2010) Intl. J. Med. Microbiol. 300:148-54). These glycopolymers play crucial roles in bacterial survival under disadvantageous conditions and in other basic cellular processes. The known WTA structures vary widely between bacterial species. S aureus TAs are composed of repetitive polyol phosphate subunits such as ribitol phosphate or glycerol phosphate.

The term "wall teichoic acid" (WTA) means anionic glycopolymers that are covalently attached to peptidoglycan via phosphodiester linkage to the C6 hydroxyl of the N-acetyl muramic acid sugars. While the precise chemical structure can vary among organisms, in one embodiment, WTA is a ribitol teichoic acid with repeating units of 1,5-phosphodiester linkages of D-ribitol and D-alanyl ester on position 2 and glycosyl substituents on position 4. The glycosyl groups may be N-acetylglucosaminyl α (alpha) or β (beta) as present in S. Aureus. The hydroxyls on the alditol/sugar alcohol phosphate repeats are substituted with cationic D-alanine esters and monosaccharides, such as N-acetylglucosamine. In one aspect, the hydroxyl substituents include D-alanyl and alpha (α) or beta (β) GlcNHAc. In one specific aspect, WTA comprises a compound of the formula:

is then composed of 11-40 ribitol-phosphate (Rbo-P) repeating units. The step-wise synthesis of WTA is first initiated by the enzyme called TagO, and S. aureus strains lacking the TagO gene (by artificial deletion of the gene) do not make any WTA. The repeating units can be further tailored with D-alanine (D-Ala) at C2-OH and/or with N-acetylglucosamine (GlcNAc) at the C4-OH position via α- (alpha) or β- (beta) glycosidic linkages. Depending of the S. aureus strain, or the growth phase of the bacteria the glycosidic linkages could be α-, β-, or a mixture of the two anomers.

Human IgG antibodies against anti-β(beta)-GlcNAc WTA mAb and anti-α(alpha)-GlcNAc WTA mAb were cloned from peripheral B cells from patients post S. aureus infection using a monoclonal antibody discovery technology which conserves the cognate pairing of antibody heavy and light chains (Meijer, P. J., et al. (2006) Journal of molecular biology 358:764-772). Individual antibody clones were expressed by transfection of mammalian cells (Meijer, P. J., et al (2009) Methods Mol Biol 525:261-277, xiv). Supernatants containing full-length IgG1 antibodies were harvested after seven days and used to screen for antigen binding by ELISA. These antibodies were positive for binding to cell wall preparations from USA300. Antibodies were subsequently produced in 200-ml transient transfections and purified with Protein A chromatography (MabSelect SuRe™, GE Life Sciences, Piscataway, N.J.)

The highest level of antibody binding was found with a human IgG1 that recognizes β(beta)-O-linked GlcNAc sugar modifications on WTA (Lehar, S. et al (2015) 527 (7578) 323-328). Less binding was achieved with monoclonal antibodies recognizing the α(alpha)-O-linked GlcNAc; an isotype control antibody against cytomegalovirus (CMV) gD protein showed some minimum reactivity due to protein A expressed on in-vivo-derived S. aureus. The antigen specificity of the antibodies was determined by genetic means, so that antibodies against α(alpha)- or β(beta)-GlcNAcs sugar modifications on WTA failed to bind to S. aureus strains lacking their respective glycosyltransferases.

Anti-WTA antibodies may be selected and produced by the methods taught in U.S. Pat. No. 8,283,294; Meijer P J et al (2006) J Mol Biol. 358(3):764-72; Lantto J, et al (2011) J Virol. 85(4):1820-33.

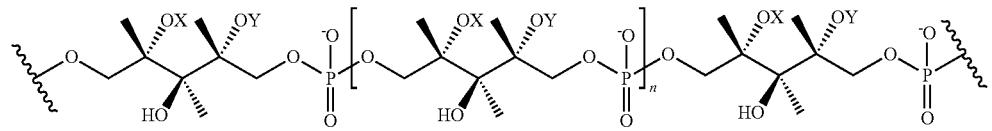

where the wavy lines indicate repeating linkage units or the attachment sites of Polyalditol-P or the peptidoglycan, where X is D-alanyl or —H; and Y is α (alpha)-GlcNHAc or β (beta)-GlcNHAc.

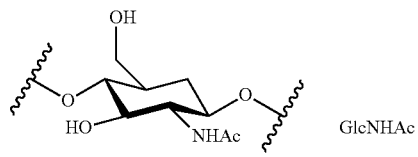

GlcNHAc

In S. aureus, WTA is covalently linked to the 6-OH of N-acetyl muramic acid (MurNAc) via a disaccharide composed of N-acetylglucosamine (GlcNAc)-1-P and N-acetylmannoseamine (ManNAc), which is followed by two or three units of glycerol-phosphates. The actual WTA polymer Cysteine amino acids may be engineered at reactive sites in an antibody and which do not form intrachain or intermolecular disulfide linkages (Junutula, et al., 2008b Nature Biotech., 26(8):925-932; Dornan et al (2009) Blood 114 (13):2721-2729; U.S. Pat. Nos. 7,521,541; 7,723,485; WO2009/052249, Shen et al (2012) Nature Biotech., 30(2): 184-191; Junutula et al (2008) Jour of Immun. Methods 332:41-52). The engineered cysteine thiols may react with linker reagents or the linker-antibiotic intermediates of the present invention which have thiol-reactive, electrophilic groups such as maleimide or alpha-halo amides to form AAC with cysteine engineered antibodies (thioMabs) and the antibiotic moiety. The location of the antibiotic moiety can thus be designed, controlled, and known. The antibiotic loading can be controlled since the engineered cysteine thiol groups typically react with thiol-reactive linker reagents or linker-antibiotic intermediates in high yield. Engineering an anti-WTA antibody to introduce a cysteine amino acid by substitution at a single site on the heavy or light chain gives two new cysteines on the symmetrical tetramer antibody. An antibiotic loading near 2 can be achieved and near homogeneity of the conjugation product AAC.

In certain embodiments, it may be desirable to create cysteine engineered anti-WTA antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as antibiotic moieties or linker-antibiotic moieties, to create an immunoconjugate, as described further herein. In certain embodiments, any one or more of the following residues may be substituted with cysteine, including V205 (Kabat numbering) of the light chain; A118 (EU numbering) of the heavy chain; and S400 (EU numbering) of the heavy chain Fc region. Nonlimiting exemplary cysteine engineered antibodies are heavy chain A118C and light chain V205C mutants of an anti-WTA antibody. Cysteine engineered anti-WTA antibodies may be generated as described (Junutula, et al., 2008b Nature Biotech., 26(8): 925-932; U.S. Pat. No. 7,521,541; US-2011/0301334.

The rifamycin-type antibiotic moiety of the antibody-antibiotic conjugates (AAC) of the invention has a cytotoxic or cytostatic effect. The rifamycins are a group of antibiotics that are obtained either naturally by the bacterium, *Nocardia mediterranei, Amycolalopsis mediterranei* or artificially. They are a subclass of the larger Ansamycin family which inhibit bacterial RNA polymerase (Fujii et al (1995) Antimicrob. Agents Chemother. 39:1489-1492; Feklistov, et al (2008) Proc Natl Acad Sci USA, 105(39): 14820-5) and have potency against gram-positive and selective gram-negative bacteria. Rifamycins are particularly effective against mycobacteria, and are therefore used to treat tuberculosis, leprosy, and *Mycobacterium avium* complex (MAC) infections. The rifamycin-type group includes the "classic" rifamycin drugs as well as the rifamycin derivatives rifampicin (rifampin, CA Reg. No. 13292-46-1), rifabutin (CA Reg. No. 72559-06-9; US 2011/0178001), rifapentine and rifalazil (Rothstein et al (2003) Expert Opin. Investig. Drugs 12(2):255-271; Fujii et al (1994) Antimicrob. Agents Chemother. 38:1118-1122; Yamane, T.; et al (1992) Chem. Pharm. Bull., 40:2707; (b) Yamane, T.; et al (1993) Chem. Pharm. Bull., 41:148-155). Many rifamycin-type antibiotics share the detrimental property of resistance development (Wichelhaus et al (2001) J. Antimicrob. Chemother. 47:153-156). Rifamycins were first isolated in 1957 from a fermentation culture of *Streptomyces mediterranei*. About seven rifamycins were discovered, named Rifamycin A, B, C, D. E. S, and SV (U.S. Pat. No. 3,150,046). Rifamycin B was the first introduced commercially and was useful in treating drug-resistant tuberculosis in the 1960s. Due to the large number of available analogues and derivatives, rifamycins have been widely utilized in the elimination of pathogenic bacteria that have become resistant to commonly used antibiotics.

Benzoxazinorifamycins are derivatives of rifamycin. Rifalazil (KRM-1648, CA Reg. No. 129791-92-0) is one example of a benzoxazinorifamycin in a class of ansamycin, rifamycin-type antibiotics developed to treat tuberculosis and other intracellular pathogens (Rothstein, D. M. et al (2003) Expert Opinion Investig. Drugs 12(2):255-271; Rothstein, D. M. et al (2006) Expert Opinion Investig. Drugs 15(6):603-623; U.S. Pat. Nos. 4,983,602; 7,342,011; 7,678, 791). Benzoxazinorifamycin derivatives of rifamycin are known for their antibacterial properties (U.S. Pat. No. 4,690, 919; EP 0190709; U.S. Pat. No. 4,983,602) and may be prepared by oxidative cyclization of an aminoresorcinol compound with rifamycin S (Yamane, T.; et al (1992) Chem. Pharm. Bull., 40:2707; (b) Yamane, T.; et al (1993) Chem. Pharm. Bull., 41:148-155).

A benzoxazinorifamycin analog IV was chosen for its high potency, its unaltered bactericidal activity in low phagolysosomal pH, its ability to withstand intracellular insults and the ease with which it could be conjugated to the antibody The compounds of the invention may exist in unsolvated as well as solvated forms with pharmaceutically acceptable solvents such as water, ethanol, and the like, and it is intended that the invention embrace both solvated and unsolvated forms.

The compounds of the invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The compounds of the invention also include isotopically-labeled compounds which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Certain isotopically-labeled compounds of the present invention (e.g., those labeled with $^3$H and $^{14}$C) are useful in compound and/or substrate tissue distribution assays. Tritiated ($^3$H) and carbon-14 ($^{14}$C) isotopes are useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C and $^{18}$F are useful for positron emission tomography (PET) studies to examine substrate receptor occupancy. Isotopically labeled compounds of the present invention can generally be prepared by following procedures analogous to those disclosed in the Examples herein below, by substituting an isotopically labeled reagent for a non-isotopically labeled reagent.

Starting materials and reagents for the preparation of intermediates for the antibody-rifamycin conjugates are generally available from commercial sources or are readily prepared using methods well known to those skilled in the art (e.g., prepared by methods generally described in Louis F. Fieser and Mary Fieser, *Reagents for Organic Synthesis*, v. 1-27, Wiley, N.Y. (1967-2013 ed.), or *Beilsteins Handbuch der organischen Chemie*, 4, Aufl. ed. Springer-Verlag, Berlin, including supplements (also available via the Beilstein online database).

The following Schemes 1-3 illustrate the chemical reactions, processes, methodology for the synthesis of Formula I, and certain intermediates and reagents, which form embodiments of the invention.

Scheme 1

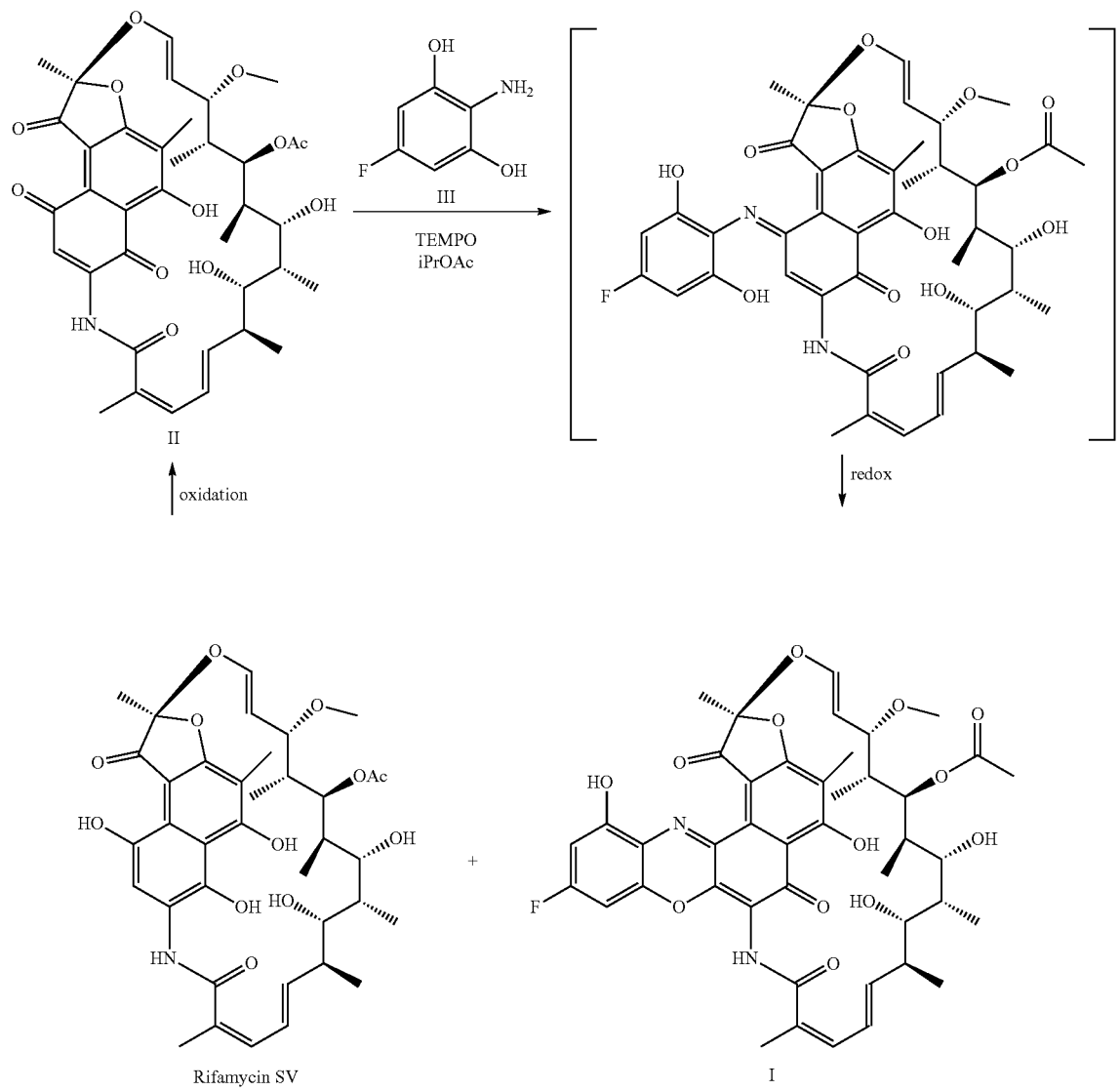

Scheme 1 shows the oxidative cyclization of Rifamycin S II with 2-amino-5-fluorobenzene-1,3-diol III to give F-benzoxazinorifamycin I. Not to be limited by any mechanism of the process, a putative imine condensation intermediate, or a tautomer thereof, leads to I and Rifamycin SV (Kump, W. et al (1973) Helv. Chim. Acta 56:2348-2377). Other oxidants besides TEMPO (Kaizer et al (2002) Jour. Mol. Cat. 180: 91-96) converted Rifamycin S II to F-benzoxazinorifamycin 1, including ambient air, oxygen gas, benzoquinone, manganese oxide ($MnO_2$), (PhI(OTs)OH, sodium periodate ($NaIO_4$), chloranil, sodium hypochlorite (NaOCl), hydrogen peroxide ($H_2O_2$), $Fe_2O_3$, $Na_2S_2O_8$, $Co(acac)_3$, $Mn(acac)_2$, $Cu(OAc)_2$, CuO, $CuBr_2$, $ZnCl_2$, $InCl_3$, $Ag(OTf)_2$, $Sc(OTf)_3$, and $Yb(OTf)_3$ in yields calculated by HPLC (Example 3) from 16% to 81%. TEMPO analogs are also effective in conversion of II to I, including 4-amino, 4-benzyloxy, 4-acetamido, and 4-hydroxyl TEMPO, 2-azaadamantane-N-oxyl (Azado, Sigma-Aldrich), and TEMPO on silica gel (Sigma-Aldrich). Other solvents besides isopropyl acetate (iPrOAc) may be used, including ethyl acetate, toluene, methanol, and tetrahydrofuran.

FIG. 1 shows a schematic of the general process for oxidative cyclization of Rifamycin S II with 2-amino-5-fluorobenzene-1,3-diol III to give F-benzoxazinorifamycin I (Scheme 1) by a semi-continuous loop process. One embodiment uses oxygen flow and TEMPO as oxidants (Example 3.3). In one embodiment, the oxygen gas comprises from about 1% to about 100% of the reaction gas phase. In one embodiment, a mixture of oxygen and nitrogen in which oxygen comprises 5 to 100 v/v % of the gas is used as oxidant. Another embodiment uses benzoquinone as oxidant (Example 3.1). The semi-continuous system assures that the oxidant and the resorcinol III are kept separated to avoid unproductive oxidation of III. Though stable as the HCl salt, 2-aminobenzene-1,3-diol, is not stable to oxygen as the free base, particularly in solution (Yamane, T.; et al (1992) Chem. Pharm. Bull., 40:2707; (b) Yamane, T.; et al (1993) Chem. Pharm. Bull., 41:148-155). Fluorination of 2-aminobenzene-1,3-diol at the 5-position as III confers greater stability. The loop system assures that Rifamycin S II produced during the oxidation is recycled to further react with additional resorcinol III. Rifamycin S II and resorcinol III are pre-mixed in the batch reactor in a solvent such as isopropyl acetate at 20-60° C. (to provide a presumed imine intermediate), which partially forms F-benzoxazinorifamycin I and Rifamycin SV (FIG. 1). Rifamycin SV is the reduced form of II. The mixture is then subjected to the oxidation loop at 0-60° C. which reforms II (from Rifamycin SV). The partial conversion mixture is then treated with further III, which consumes more of the reformed Rifamycin S II to give I and Rifamycin SV. The mixture is subjected to the oxidation loop and the addition of resorcinol until the reaction is deemed completed. Resorcinol III can be added in a stepwise or in a continuous mode. At the end of the reaction the mixture is extracted with a water solution of ascorbic acid and then with water. The organic phases are evaporated to dryness and the residue dissolved in DCM/MeOH and chromatographed over silica gel. The product is then recrystallized from MeOH/water.

Separation of the two reaction segments allows (a) efficient conversion of II and III to an intermediate in the continuous stirred tank followed by redox step involving formation of I and Rifamycin SV and b) oxidation of Rifamycin SV to II in the plug flow column to avoid oxidative consumption of III. The reaction is progressed through multiple cycles to complete the conversion of II to I.

In one embodiment, a double jacket glass reactor is connected via a T-junction to a flow reactor with static mixing elements (Example 3.4). The third end of the T-junction is connected to a pump dosing the oxidant solution. The outlet of the flow reactor is connected with the double jacket glass reactor. Reagents II and III are mixed in the glass reactor with iPrOAc at about 20-60° C. overnight. The solution is pumped over the flow reactor together with the oxidant solution. The flow reactor is kept at an outlet temperature of about −5 to 5° C. The outlet solution is pumped back in the double jacket glass reactor (loop process). The loop is run over a period of about 8 h. Resorcinol is then added into the glass reactor and reacted overnight (cycle 1). The loop process is restarted. A total of three cycles are performed.

In another embodiment, a jacketed glass vessel is connected via a T-junction to the flow reactor and the oxidant feed in a batch-continuous loop process reaction (Example 3.3). The flow reactor is connected to a gas/liquid separation flask via a cooling coil. The separation flask is connected to the jacketed glass vessel. A filter is placed between the separation flask and the jacketed vessel. The liquid portion of the oxidation loop is pumped back into the cooling vessel by the aid of a peristaltic pump. A sampling valve is placed directly after this pump. Resorcinol solution is fed into the jacketed glass reactor. The oxygen flow is controlled by a gas mass flow controller. In the jacketed glass reactor, Rifamycin S II and TEMPO are dissolved in isopropylacetate (iPrOAc) and the vessel temperature set at about 50° C. The resorcinol III solution in isopropyl acetate is fed into the vessel for 60 min while mixing. Then the mixture is pumped through the flow reactor together with oxygen at 60° C. and the loop process started while keeping the resorcinol feed constant. The loop is run for about 6-8 h.

Scheme 2

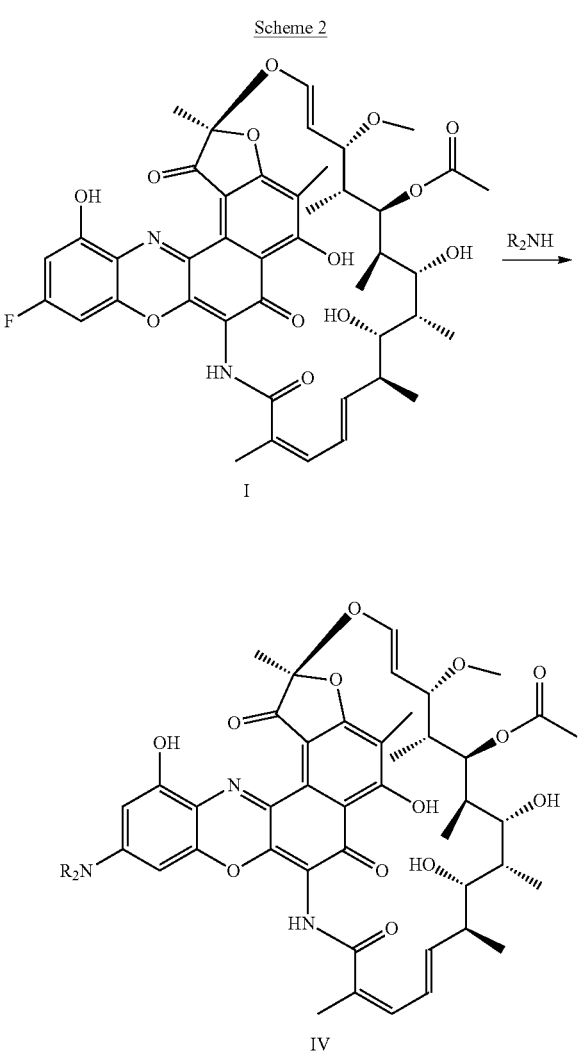

Scheme 2 shows nucleophilic substitution of fluoride substituent from F-benzoxazinorifamycin I with a secondary amine, $R_2NH$ where R is independently selected from various alkyl and cyclic substituents to give amino-benzoxazinorifamycin analogs IV. Secondary amines, $R_2NH$, include but are not limited to dimethylamine, diethylamine, di-n-propylamine, 1-methylpiperazine, N1-isobutylpiperazine, and N,N-dimethylpiperidin-4-amine. Benzoxazinorifamycin analog IV replaces the N-isobutylpiperazine group of rifalazil at the 5' position (following the convention of U.S. Pat. No. 7,547,692 at column 13) with tertiary amines, including N,N-dimethylpiperidin-4-amine (U.S. Pat. Nos. 7,265,107; 7,271,165; 7,884,099).

Scheme 3

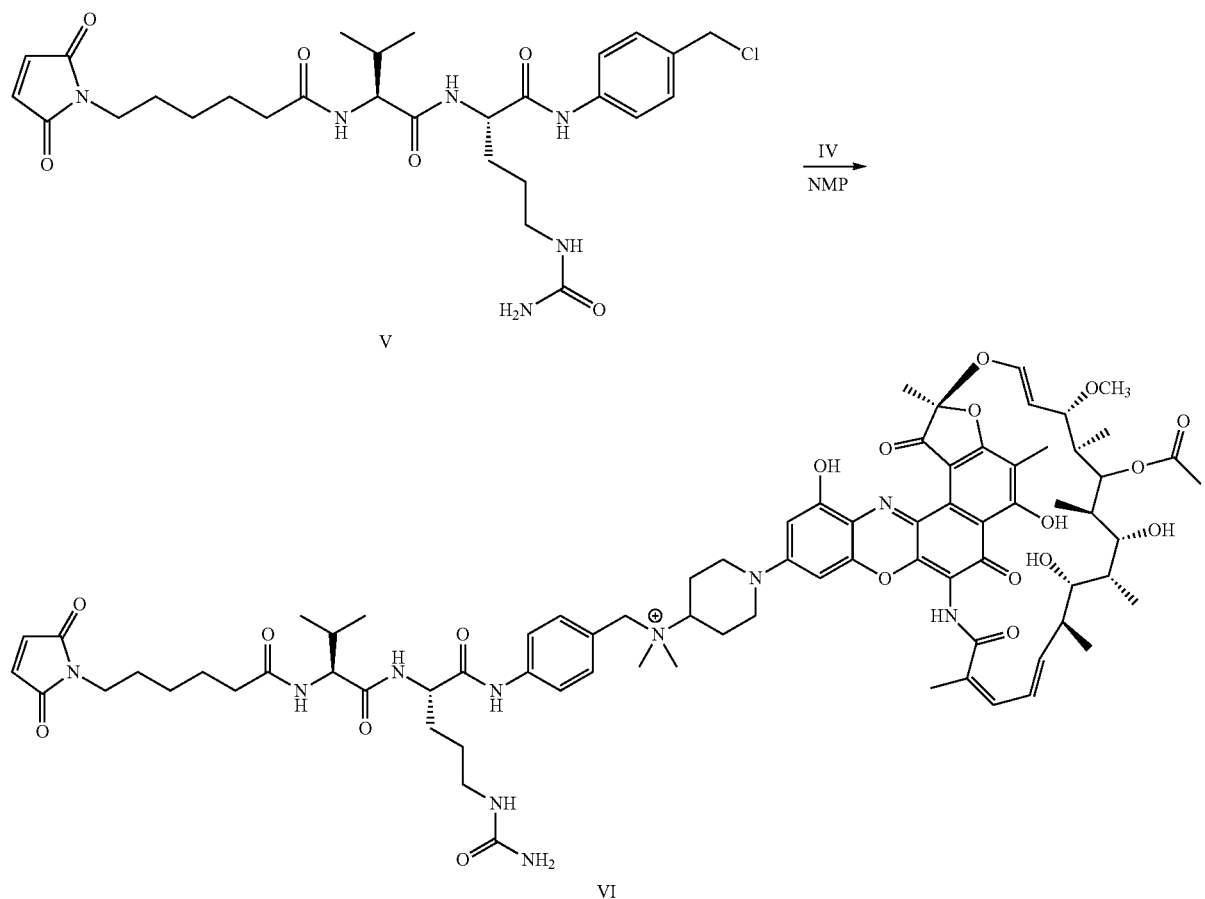

Scheme 3 shows alkylation of linker chloride V with tertiary amine rifalazil analog IV to give linker-antibiotic VI.

EXAMPLES

Example 1 (((5-fluoro-2-nitro-1,3-phenylene)bis(oxy))bis(methylene))dibenzene

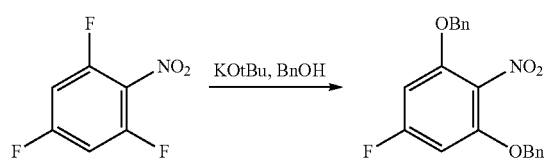 [SMILES: O=[N+]([O-])c1c(F)cc(F)cc1F ; O=[N+]([O-])c1c(OCc2ccccc2)cc(F)cc1OCc1ccccc1]

To a suspension of potassium tert-butoxide (66.5 g, 593 mmol) in THF (300 ml) was added dropwise over a period of 20 min a solution of phenylmethanol (benzyl alcohol, 66.3 g, 613 mmol) in THF (60 ml) resulting in a yellow solution. Other alkoxide reagents can be used such as sodium tert-butoxide, potassium isopropoxide, sodium isopropoxide, potassium ethoxide, sodium ethoxide, potassium methoxide, and sodium methoxide. Alternatively, other ether solvents such as 2-methyltetrahydrofuran or diisopropyl ether can be used. Alternatively, phenylmethanol can be added to a 1M solution of lithium hexamethyldisilazane (LiHMDS) in THF over a period of 2 h (two hours) at an internal temperature of 1-4° C. This yellow solution was added dropwise via teflon cannula over a period of 1 h to a clear solution of 1,3,5-trifluoro-2-nitro benzene, CAS Reg. No. 315-14-0 (50.0 g, 282 mmol) in 2-Me-THF (400 ml) at in internal temperature of 0-10° C. and the resulting orange-red solution was stirred at 0-5° C. for 1 h. Alternatively, 1,3,5-trifluoro-2-nitro benzene can be dissolved in THF. Then water (500 ml) and NaCl solution (30 ml, saturated) were added and the phases were separated. The water phase was extracted with 2-Me-THF (250 ml) whereas the organic phase was washed with brine (600 ml). Alternatively, the water phase can be extracted with dichloromethane. The organic phases were combined dried over $Na_2SO_4$ and the yellow clear solution was concentrated under vacuum until the crystallization of the product started. Then, 2-Me-THF (150 ml) and EtOH (500 ml) were added and the suspension was stirred in an ice bath for 3 h. The crystals were filtered off, washed with ice-cold n-heptane (200 ml) and dried under vacuum until weight constancy to yield (((5-fluoro-2-nitro-1,3-phenylene)bis(oxy))bis(methylene))-dibenzene, CAS Reg. No. 1639352-18-3 (91.6 g, 89.90/% based on 1,3,5-trifluoro-2-nitro benzene) as a light yellow solid. m.p.: 117.8-119.4° C. $^1$H-NMR (CDCl$_3$): δ 7.44-7.27 (, 10H), 6.37 (d, J=10.2 Hz, 2H), 5.18-5.06 (m, 4H). MS (ESI): 352.1 [M-H]$^-$. Anal. calc. for $C_{20}H_{16}FNO_4$: C, 67.98, H, 4.56, N, 3.96; found C, 67.89, H, 4.50, N, 3.94.

Example 2 2-Amino-5-fluoro-benzene-1,3-diol III

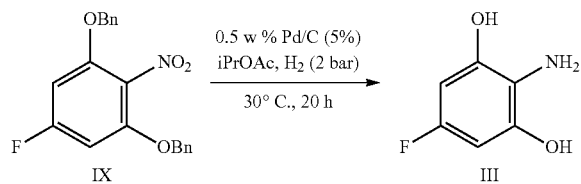

A 50 liter autoclave was loaded sequentially with (((5-fluoro-2-nitro-1,3-phenylene)bis(oxy))bis(methylene))-dibenzene IX, CAS Reg. No. 1639352-18-3 (3.0 kg, 8.49 mol), Pd/C E101 N/D, 5% Pd catalyst (15 g) and iPrOAc (829 kg) the autoclave was purged with Ar and then with hydrogen gas ($H_2$). The Pd/C catalyst may be matrix activated carbon, wet support, Degussa type E101 NE/W, E101 N/D, E105R/W (Evonik Industries, Johnson Matthey), Type 128M (Evonik Industries), 5207 Escat 162 (BASF), Noblyst® P1070 or Noblyst® P1090 (Evonik Industries). Other heterogeneous metal catalysts can be used for reduction of the benzyl and nitro groups such as palladium, platinum, or ruthenium on carbon or alumina support. Then the hydrogen pressure was adjusted to 2 bar and the reaction mixture was heated under stirring to 28-32° C. and hydrogenated at this temperature for 21 h. The reaction mixture was cooled to ambient temperature and the pressure was carefully released. The reaction may be conducted in two or more stages, isolating partially reduced nitro or benzyl intermediates such as 5-fluoro-2-nitrobenzene-1,3-diol, and further treatment with hydrogen gas and a heterogeneous metal catalyst to yield III.

The reaction mixture was filtered under Ar, the autoclave and the filter were washed with iPrOAc the crude hydrogenation solution was combined with the product solutions of two analogous hydrogenation runs. The solvent was then partially removed under vacuum whereupon the product started to precipitated. Then, n-heptane (40 l) was added, the suspension was cooled to 0-5° C. and stirred at this temperature for 18 h. The suspension was transferred into a pre-cooled (0-5° C.) filter drier, the crystals were washed with n-heptane (15 l, cooled) and dried under to yield 2-amino-5-fluoro-benzene-1,3-diol III, CAS Reg. No. 16393406-55-5 (3.0 kg, 81.9% based on starting material) as a beige solid. $^1$H-NMR ($d_6$-DMSO): δ 10.18-7.54 (m, 1H), 6.05 (d, J=7.0 Hz, 2H), 3.96 (br d, J=10.4 Hz, 1H). $^{13}$C-NMR ($d_6$-DMSO): δ 154.6 (d, J=230.3 Hz, IC), 145.4, 145.3, 120.3, 99.6, 99.1. MS (EI$^+$): m/z 143.0 (M$^+$, 100%). Anal. calc. for $C_6H_6FNO_2$: C, 50.35, H, 4.23, N, 9.79; found C, 50.36, H, 4.33, N, 9.72.

Alternatively, the reduction of IX can be stopped to isolate the debenzylated, nitro diol intermediate, 5-fluoro-2-nitrobenzene-1,3-diol:

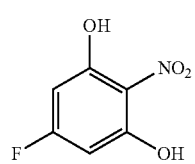

as an orange solid in near quantitative yield and >95% purity by GC analysis. $^1$H-NMR (d6-DMSO) δ 11.20 (s, 2H), 6.24 (d, 2H). Anal. calcd. for $C_6H_4FNO_4$: C, 46.63, H, 2.33, N, 8.09; found C, 41.58, H, 2.52, N, 8.04. 5-Fluoro-2-nitrobenzene-1,3-diol was reduced to III by heterogeneous hydrogenation with a broad range of carbon-dispersed palladium, platinum, platinum-vanadium, and nickel heterogeneous metal catalysts including Pt/C, Pt.V/C, Ra—Ni (Rainey Nickel), and Ra—Co.

Example 3 F-benzoxazinorifamycin I 3.1 Full Batch Process with Benzoquinone

In a 500 ml glass reactor Rifamycin S II, commercially available from ChemShuttle Inc., Fremont, Calif., U.S. Pat. Nos. 7,342,011; 7,271,165; 7,547,692 (13.92 g, 20 mmol), 2-amino-5-fluorobenzene-1,3-diol III (4.9 g, 34 mol, 1.6 eq) and benzoquinone (2.38 g, 24 mmol, 1.2 eq) are dissolved in iPrOAc (185 mL). The solution is stirred for 40 h at 25° C. The solution is polish filtered and then the filtrate is evaporated to dryness obtaining 25.3 g of crude F-benzoxazinorifamycin 1(29.2% yield, 18.930/% assay). MS (EI$^+$): m/z 817.6 (M$^+$, 15%). HPLC (Method A): 5.32 min.

HPLC Method A:

Sample preparation: 50 mg substance in 100 ml Acetonitrile

System: Agilent 1200, binary
Eluent A: ACN/$H_2$O 9:1+0.25% TFA
Eluent B: ACN/$H_2$O 1:9+0.25% TFA
Column: x-Bridge C18 4.6×50 mm, 2.5 μm
Flow: 1.5 ml/min
Injection: 10 μl
λ: 220 nm
Column temperature: 40° C.
Gradient:

| Time [min] | A [%] | B [%] |
|---|---|---|
| 0.00 | 17.5 | 82.5 |
| 6.00 | 95 | 5 |
| 7.00 | 95 | 5 |

Postime: 3 min 3.2 Batch Process with Benzoquinone

In a 500 ml glass reactor Rifamycin S II (20.0 g, 29 mmol), 2-amino-5-fluorobenzene-1,3-diol III (4.9 g, 35 mmol, 1.2 eq) are dissolved in iPrOAc (300 mL). The solution is stirred overnight at 25° C. The solution is then cooled to −5.0° C. and an iPrOAc solution of benzoquinone (1.86 g, 17 mmol, 0.6 eq, in 45 mL solvent) is added over 8 h. Then additional resorcinol (2.5 g, 17 mmol, 1.2 eq) is added at 25° C. and the mixture reacted overnight. After this time an iPrOAc solution of benzoquinone (0.93 g, 9 mmol, 0.3 eq in 22.5 mL) is added over 4 h. The sequential addition of resorcinol and benzoquinone is repeated a total of three cycles according to the following:

| Cycles n. | Amount III | Amount benzoquinone | Dosing time |
|---|---|---|---|
| 1 | 2.5 g | 1.86 g | 8 h |
| 2 | 1.2 g | 0.93 g | 4 h |
| 3 | 0.6 g | 0.93 g | 4 h |

Once the cycles are completed the reaction mixture is extracted with an aqueous solution of ascorbic acid (100 ml, 10% w/w) and then extracted three times with water (100 ml). The organic phase is evaporated to dryness obtaining 33.7 g of crude F-benzoxazinorifamycin I (73.1% yield, 51.0% assay) as a black foam. MS (EI+): m/z 817.6 (M+, 89%). HPLC (Method A): 5.34 min.

3.3 Batch Process with Oxygen Gas and TEMPO

In a 1.5 L glass reactor Rifamycin S II (40.0 g, 58 mmol), 2-amino-5-fluorobenzene-1,3-diol III (20.6 g, 144 mmol, 2.5 eq) are dissolved in iPrOAc (600 mL). The mixture is stirred for 2 h at 60° C. under Argon. After this time, 2,2,6,6-Tetramethyl-1-piperidinyloxy, free radical, TEMPO (Kaizer et al (2002) Jour. Mol. Cat. 180:91-96) (0.90 g, 5.8 mmol, 0.1 eq) is added and the argon replaced by an oxygen gas O2 (5 v/v 0% in $N_2$) flow (400 mL/min). The reaction mixture is stirred at 60° C. for 22 h. The mixture is allowed to cool to room temperature and is hence filtered on a paper filter. The filter is washed with ethyl acetate (300 mL). The filtrate is collected and extracted with an aqueous solution of $Na_2S_2O_3$ (10% w/w, 100 mL) and brine (100 mL). The organic phases are collected and evaporated to dryness. The residue is dissolved in DCM with 2% v/v MeOH (150 mL) and chromatographed over Silica Gel (250 g, eluent: DCM with 2% v/v MeOH). The fractions containing the product are evaporated to dryness to give 22.3 g of F-benzoxazinorifamycin I (45% yield, 95% assay) as dark red solid. 1H NMR (600 MHz, CHCl$_3$): δ 14.42-14.33 (m, 1H), 10.29-10.00 (m, 1H), 6.77-6.62 (m, 1H), 6.58-6.48 (m, 1H), 6.39-6.35 (m, 1H), 6.10-4.60 (m, 4H), 4.04-3.90 (m, 1H), 3.61 (s, 1H), 3.50 (s, 1H), 3.35 (s, 1H), 3.11 (s, 1H), 2.33 (s, 1H), 2.29 (s, 1H), 2.23 (s, 2H), 2.16-2.11 (m, 6H), 2.05 (d, J=18 Hz, 2H), 1.78 (d, J=12 Hz, 2H), 1.58-1.54 (m, 6H), 1.37-0.51 (m, 13H). HRMS: m/z 818.3061 (calculated mass: 818.3062). HPLC (Method B): 5.86 min.

HPLC Method B:
Sample preparation: 2 mg substance in 1 ml Acetonitrile
System: Agilent 1200, binary
Eluent A: H$_2$O
Eluent B: ACN
Eluent C: TFA 0.1% in H$_2$O
Column: x-Bridge C18 4.6×50 mm, 2.5 μm
Flow: 1.5 ml/min
Injection: 2 μl
λ: 220 nm
Column temperature: 40° C.
Gradient:

| Time [min] | A [%] | B [%] | C [%] |
|---|---|---|---|
| 0.00 | 75 | 20 | 5 |
| 6.00 | 10 | 85 | 5 |
| 9.00 | 10 | 85 | 5 |

3.4 Loop Process with Benzoquinone

A double jacket glass reactor is connected via a T-junction to a flow reactor with static mixing elements. The third end of the T-junction is connected to a pump dosing the oxidant solution. The outlet of the flow reactor is connected with the double jacket glass reactor. In a 18 L glass reactor, Rifamycin S II (200.4 g, 288 mmol) and 2-amino-5-fluorobenzene-1,3-diol III (49.5 g, 347 mmol, 1.2 eq) are dissolved in iPrOAc (3.0 L). The solution is stirred overnight at 25° C. Alternatively, II and III are mixed in the glass reactor with iPrOAc at 20-60° C. overnight. Then, the solution is pumped (5.2 L/h) over the flow reactor together with a solution of benzoquinone in iPrOAc (see table for details) over a structured-mixer-flow reactor (V=130 ml) at −5.0 to 5.0° C. The resulting solution is then pumped back to the batch reactor which is kept at 25° C. The loop process is run during the benzoquinone dosing time (see table). Afterwards, additional resorcinol (24.7 g, 173 mmol, 0.6 eq) is added at 25° C. and the mixture is reacted overnight. The sequential addition of benzoquinone and resorcinol is repeated a total of three times according to the following table.

| Cycle n. | Amount III | Amount benzoquinone | Dosing time |
|---|---|---|---|
| 1 | 24.7 g | 18.7 g | 10 h |
| 2 | 12.4 g | 9.3 g | 8 h |
| 3 | 6.2 g | 9.3 g | 8 h |

Once the cycles are completed, the reaction mixture is extracted with an aqueous solution of ascorbic acid (1.0 L, 10% w/w) and then extracted three times with water (1.0 L). The organic phase is evaporated to dryness. The residue is dissolved in DCM with 2% v/v MeOH (2.0 L) and chromatographed over Silica Gel (3.0 kg, eluent: DCM with 2% v/v MeOH, 32 L). The fractions containing the product are evaporated to dryness. 186.4 g of product (81.5% yield, 85.5% assay) are obtained as a black foam. The foam is dissolved in Methanol (8.0 L) at 40° C. then water (4.8 L) is added over 4 h. The suspension is held for 2 h at 40° C. then it is cooled to 0° C. during 8 h and held at this temperature for 2 h. The suspension is filtered and washed with a solution of water (0.5 L) and methanol (0.3 L) and twice with water (0.8 L). The black crystals are dried for 40 h in a vacuum compartment dryer at 10 mbar. 148.8 g of F-benzoxazinorifamycin I as dark red crystals are obtained (63.4%0 yield, 97.4% assay). 1H NMR (600 MHz, CHCl$_3$): δ 14.42-14.33 (m, 1H), 10.29-10.00 (m, 1H), 6.77-6.62 (m, 1H), 6.58-6.48 (m, 1H), 6.39-6.35 (m, 1H), 6.10-4.60 (m, 4H), 4.04-3.90 (m, 1H), 3.61 (s, 1H), 3.50 (s, 1H), 3.35 (s, 1H), 3.11 (s, 1H), 2.33 (s, 1H), 2.29 (s, 1H), 2.23 (s, 2H), 2.16-2.11 (m, 6H), 2.05 (d, J=18 Hz, 2H), 1.78 (d, J=12 Hz, 2H), 1.58-1.54 (m, 6H), 1.37-0.51 (m, 13H). HRMS: m/z 818.3069 (calculated mass: 818.3062). HPLC (Method A): 5.35 min.

3.5 Batch Process with TEMPO

A reactor was charged with i-PrOAc (355 g), Rifamycin S II (40.0 g, 57.5 mmol) and 2,2,6,6-Tetramethyl-1-piperidinyloxy, free radical (TEMPO) (9.0 g, 57.6 mmol) under nitrogen gas. The reactor contents were warmed to 60° C. for 1 h, followed by charging 2-amino-5-fluoro-benzene-1,3-diol III (8.0 g, 55.9 mmol) as a solution in i-PrOAc (266 g) over 1 h. Further TEMPO (9.0 g, 57.6 mmol) was added and the mixture stirred at 60° C. for 1 h. Additional 2-amino-5-fluoro-benzene-1,3-diol III (8.0 g, 55.9 mmol) was charged as a solution in i-PrOAc (266 g) over 1 h, followed by stirring at temperature for 2 h. Further TEMPO (1.8 g, 11.5 mmol) in i-PrOAc (10 g) was added and the mixture stirred at 60° C. for 1 h. Additional 2-amino-5-fluoro-benzene-1,3-diol III (1.6 g, 11.2 mmol) was charged as a solution in i-PrOAc (60 g) over 1 h, followed by mixing for 2 h. A final charge of 2-amino-5-fluoro-benzene-1,3-diol III (1.6 g, 11.2 mmol) was added as a solution in i-PrOAc (60 g) over 1 h, followed by mixing at 60° C. for 2 h.

The batch was concentrated under vacuum distillation to 50% of the volume. After cooling to 20-25° C., heptane (410 g) was charged and the mixture filtered through a pad of silica (160 g), covered by a pad of Celite® (40 g). The pad was washed with 1:1 heptane/i-PrOAc (943 g) and the combined filtrate concentrated to 5% of the volume. Once cooled to 20-25° C., i-PrOAc (71 g) was charged, followed by heptane (129 g) over 1 h. The contents were stirred at 20-25° C. for 3 h before filtering the slurry. The cake was washed with 3:1 heptane/i-PrOAc (39 g) before being transferred to a new reactor. The wet material was dissolved in i-PrOAc (73 g) and stirred at 20-25° C. for 1 h before the addition of by heptane (129 g) over 1 h. The contents were stirred at 20-25° C. for 3 h before filtering the slurry and washing the cake with 3:1 heptane/i-PrOAc (39 g). The final wet cake was dried under vacuum to deliver F-benzoxazinorifamycin 1 (23.5 g, 50.0% yield). $^1$H NMR (600 MHz, Benzene-d$_6$:Chloroform-d, 3:1, 60° C.) δ 14.59 (s, 1H), 10.41 (s, 1H), 7.76 (s, 1H), 7.18 (p. J=1.1 Hz, 1H), 6.46 (dd, J=10.3, 2.5 Hz, 2H), 6.29 (dd, J=9.0, 2.4 Hz, 1H), 6.22-6.13 (m, 1H), 5.94 (d, J=10.7 Hz, 1H), 5.59 (s), 5.16 (d, J=7.0 Hz, 1H), 5.11 (dd, J=12.3, 7.7 Hz, 1H), 3.76-3.60 (m, 1H), 3.44 (d, J=9.0 Hz, 1H), 3.13 (dd, J=7.7, 5.6 Hz, 1H), 3.03-2.94 (m, 1H), 2.89 (s, 4H), 2.34 (s, 3H), 2.15-2.06 (m, 1H), 2.04 (d, J=1.4 Hz, 3H), 1.65 (s, 3H), 1.57 (dddd, J=14.1, 12.0, 6.9, 3.2 Hz, 3H), 0.94 (d, J=7.0 Hz, 3H), 0.65 (d, J=6.8 Hz, 3H), 0.43 (s, 5H), 0.43-0.32 (m, 4H). $^{13}$C NMR (151 MHz, C$_6$D$_6$:CDCl$_3$ 3:1, 60° C.) δ 193.8, 184.4, 174.3, 171.8, 168.9, 168.3, 166.6, 158.1, 158.0, 144.9, 144.8, 143.4, 141.8, 140.6, 133.3, 131.6, 126.4, 120.1, 115.6, 114.8, 113.2, 112.7, 108.1, 107.8, 99.7, 99.5, 94.9, 94.7, 79.1, 78.4, 73.8, 73.4, 56.3, 41.3, 40.2, 37.3, 33.2, 22.2, 20.8, 20.4, 16.9, 11.2, 11.0, 7.7.

Example 4 Dimethylaminopiperidyl rifa IVa

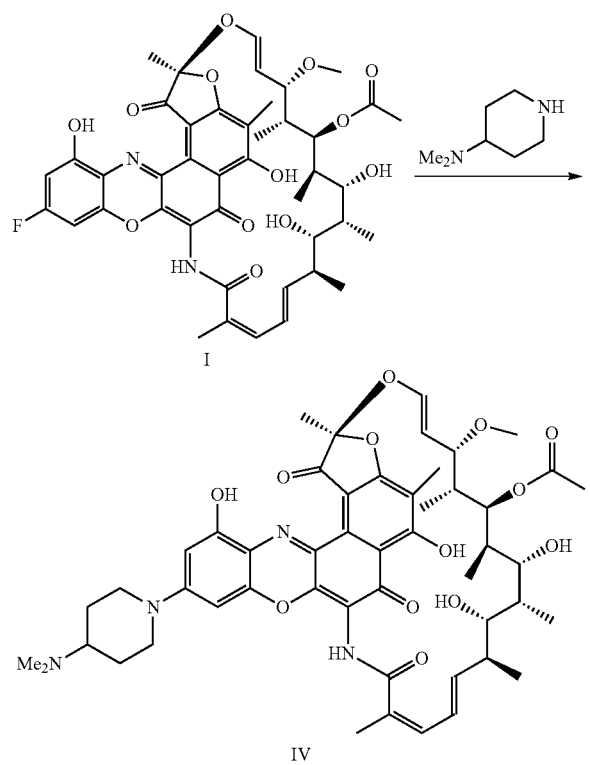

Dry THF (135 g) and F-rifa I (10.0 g, 12.2 mmol) were charged to the reactor under N$_2$. The reactor contents were cooled to 0-5° C. before N,N-dimethylpiperidin-4-amine (2.3 g, 17.9 mmol) was charged over 0.5 h while maintaining an internal temperature of ≤5° C. After the addition, the reactor contents were warmed to 20-25° C. and held for 2 h. EtOAc (135 g) was charged and the mixture agitated for 0.5 h. The contents were filtered and washed with EtOAc (25 g). The combined filtrates were distilled under vacuum to 25 mL volume. After cooling to 20-25° C., EtOAc (185 g) was charged, followed by 70/% aq. NaHCO$_3$ solution (45 g), 25% aq. NaCl solution (45 g), and purified water (45 g). After phase separation, the aqueous layer was removed and 25% aq. NaCl solution (45 g) and purified water (45 g) were added to the organic phase. The aq. layer was removed and the organic layer subjected to treatment with 7% aq. NaHCO$_3$ solution (45 g), 25% aq. NaCl solution (45 g), and purified water (45 g). After phase separation, the aqueous layer was removed and 25% aq. NaCl solution (45 g) and purified water (45 g) were added to the organic phase. The organic phase was filtered and the filtrate concentrated to 25 mL volume prior to dilution with heptane (90 g). Further concentration to 25 mL volume was followed by dilution with heptane (90 g) and a final concentration to 25 mL volume. Filtration of the suspension and washing of the cake with heptane (2×20 g) gave a solid, which once dried under vacuum to give dimethylaminopiperidyl rifa IVa (10.6 g, 93.5% yield). $^1$H NMR (600 MHz, Toluene-d$_8$) δ 16.53 (s, 1H), 11.59 (s, 1H), 9.86 (s, 1H), 7.35 (s, 1H), 6.47-6.32 (m, 1H), 6.21 (d, J=11.9 Hz, 1H), 5.87 (s, 1H), 5.62 (s, 1H), 5.44 (d, J=11.4 Hz, 1H), 5.30-5.18 (m, 1H), 4.87 (dd, J=14.6, 10.0 Hz, 1H), 3.58 (d, J=7.7 Hz, 1H), 3.26-3.11 (m, 2H), 3.03 (d, J=10.9 Hz, 1H), 2.91 (d, J=12.1 Hz, 1H), 2.73 (s, 3H), 2.64 (s, 3H), 2.28 (s, 2H), 2.24 (s, 3H), 2.15 (s, 3H), 2.04 (s, 6H), 2.00 (s, 1H), 1.97-1.89 (m, 1H), 1.79 (d, J=28.4 Hz, 2H), 1.66 (s, 3H), 1.64 (s, 5H), 1.17 (d, J=6.9 Hz, 6H), 0.78 (d, J=6.3 Hz, 3H), 0.49 (d, J=6.5 Hz, 5H). $^{13}$C NMR (151 MHz, Tol) δ 193.0, 182.6, 175.7, 175.1, 171.5, 171.2, 158.0, 157.2, 146.4, 145.2, 144.5, 142.2, 131.5, 131.0, 130.9, 128.9, 128.0, 119.6, 114.0, 112.6, 111.5, 109.4, 107.7, 106.3, 95.0, 92.9, 79.9, 79.0, 74.8, 73.8, 61.5, 55.2, 47.0, 46.4, 44.1, 42.4, 42.3, 37.3, 33.1, 29.2, 29.0, 23.6, 23.1, 21.4, 16.4, 13.2, 13.0, 11.7, 8.5.

Example 5 N—((S)-1-(((S)-1-((4-(chloromethyl)phenyl)amino)-1-oxo-5-ureidopentan-2-yl)amino)-3-methyl-1-oxobutan-2-yl)-6-(2,5-dioxo-2,5-dihydro-1H-pyrrol-1-yl)hexanamide V Dry N-methylpyrrolidone, NMP (55 g) and 6-(2,5-dioxo-2,5-dihydro-1H-pyrrol-1-yl)-N—((S)-1-(((S)-1-((4-(hydroxymethyl)phenyl)amino)-1-oxo-5-ureidopentan-2-yl)amino)-3-methyl-1-oxobutan-2-yl)hexanamide, MC-VC-PAB-OH (10.0 g 17.5 mmol) were charged to the reactor under N$_2$.

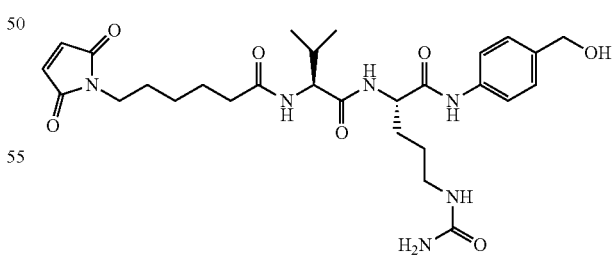

MC-VC-PAB-OH

The contents were warmed to 50-55° C. for 1 h before cooling to 0-5° C. Thionyl chloride (2.6 g, 21.9 mmol) was charged to the reactor over 1 h with temperature of ≤5° C. After the addition, the reactor contents were warmed to 20-25° C. and held for 1 h. Since LC showed starting material remaining, the batch was cooled to 0-5° C. and more thionyl chloride (0.2 g, 1.7 mmol) was charged to the reactor over 1 h. After the addition, the contents were warmed to 20-25° C. and held for 1 h. The batch was cooled to 0-5° C. and water (170 g) was added while maintaining temperature of ≤5° C. The resultant slurry was filtered and the filter cake washed with water (2×30 g). The cake was then washed with EtOAc (30 g), CH$_3$CN (2×30 g) and MTBE (1×30 g). The wet cake was dried under vacuum at 20-25° C. to give a lightly colored solid (8.3 g, 80% yield). $^1$H NMR (600 MHz, DMSO-d6, 28° C.) δ 10.02 (s, 1H), 8.06 (d, 7.5, 1H), 7.78 (d 8.7, 1H), 7.60 (d, 8.6, 2H), 7.36 (d, 8.6, 2H), 6.99 (s, 2H), 5.98 (bs, 1H), 5.40 (vbs, 1H), 4.71 (s, 2H), 4.38 (m, 1H), 4.19 (dd, 0.5, 6.9, 1H), 3.37 (t, 7.1, 2H), 3.03 (m, 1H), 2.94 (m, 1H), 2.18 (m, 1H), 2.12 (m, 1H), 1.97 (m, 1H), 1.70 (m, 1H), 1.60 (m, 1H), 1.48 (m, 5H), 1.37 (m, 1H), 1.19 (pen, 7.7, 2H), 0.85 (d, 6.8, 3H), 0.82 (d, 6.8, 3H). $^{13}$C NMR (151 MHz, DMSO-d6, 28 deg C.) δ 172.2, 171.2, 170.9, 170.6, 158.8, 138.9, 134.3, 132.2, 129.4, 119.0, 57.5, 53.0, 46.1, 38.5, 36.9, 34.8, 30.3, 29.2, 27.7, 26.7, 25.7, 24.8, 19.1, 18.1.

Example 6 Linker-antibiotic VI

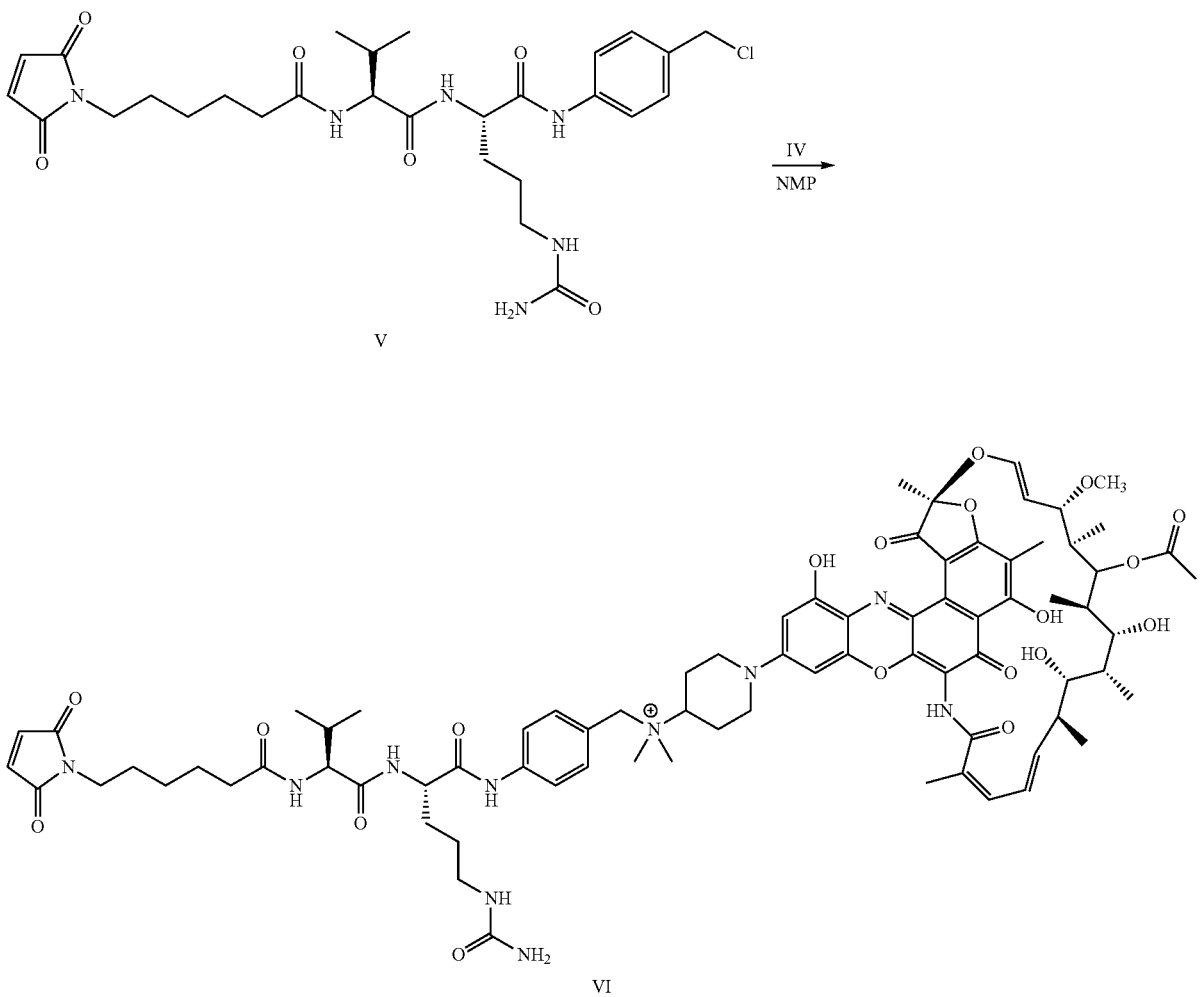

To the reactor were charged NMP (495 g), dimethylaminopiperidyl rifa IVa (90.0 g, 97.1 mmol) and N—((S)-1-(((S)-1-((4-(chloromethyl)phenyl)amino)-1-oxo-5-ureidopentan-2-yl)amino)-3-methyl-1-oxobutan-2-yl)-6-(2,5-dioxo-2,5-dihydro-1H-pyrrol-1-yl)hexanamide V (60.0 g, 101.5 mmol) under N$_2$. The contents were heated to 55-60° C. for 12 h. After cooling, EtOAc (1.2 kg) was charged and the contents aged for 4 h. The slurry was filtered and the cake washed with EtOAc (158 g). The filter cake was dried under vacuum at 20-25° C. to provide crude linker-antibiotic VI as a dark blue solid (137.1, 93% yield).

Purification: Crude linker-antibiotic VI (113.3 g) was dissolved in 1:1 acetonitrile (ACN)/water with 0.05% formic acid (FA) (8.5 L). The solution was filtered through Celite® (200 g) and the filtrate treated with 0.05% FA in water (34.0 L). The diluted solution was charged to the pre-equilibrated column followed by elution with the following mobile phase composition:

| Eluent | % Composition (ACN/water/FA) | Flow Rate (L/min) | Time (min) | Fractions collected (number × L) |
|---|---|---|---|---|
| 1 | 10/90/0.05 | 4.0 | 79 | — |
| 2 | 30/70/0.05 | 3.9 | 128 | 19 × 25 |
| 3 | 40/60/0.05 | 3.9 | 83 | 47 × 5 |
| 4 | 90/10/0.05 | 3.9 | 53 | — |
| 5 | 50/50/0.05 | 3.9 | 58 | — |
| 6 | 10/90/0.05 | 3.9 | 73 | — |

The column was packed with HP20 SS resin (DIAION™ HP20SS, Mitsubishi Chemical) composed of highly cross-linked, hydrated polystyrene; 30-70% benzene, diethenyl-, polymer with ethenylbenzene and ethenylethylbenzene. The concentration step commenced by first diluting the crude linker-antibiotic VI solution with 0.05% FA in water (165 L) to achieve a composition of ACN/H$_2$O/FA: 10/90/0.05. The diluted solution was then charged to the pre-equilibrated resin (10/90/0.05) at a rate of 0.8 L/min. Elution continued with 90/10/0.05 at 0.8 L/min for 37 min. The product was collected when the blue band began eluting off the column and all blue material was collected into one fraction. Purity of the capture fraction was 94.4% (~10 L). The column was rinsed with 60:40 MeOH/water (22.4 L).

The fraction containing product linker-antibiotic VI was concentrated in vacuo at a maximum temperature of 25° C. until no more solvent (ACN) was observed condensing. The concentrate was transferred and the distillation flask rinsed with water for injection (WFI, 0.5 L). The diluted concentrate was polish-filtered and the filtrate lyophilized to give the purified linker-antibiotic VI as a dark blue solid (45.6 g, 40.2% yield). $^1$H NMR (600 MHz, CD$_2$Cl$_2$:d4-MeOH 9:1, 4 deg C.) δ 7.80 (d, 8.4, 2H), 7.42 (d, 8.3, 2H), 6.74 (dd, 15.9, 11.2, 1H), 6.69 s, 2H), 6.52 (s, 1H), 6.39 (s, 1H), 6.34 (d, 10.6, 1H), 6.17 (d, 12.8, 1H), 6.15 (dd, 15.9, 7.5, 1H), 4.96 (dd, 12.7, 7.5, 1H), 4.86 (d, 10.8, 1H), 4.49 (dd, 9.6, 4.0, 1H), 4.46 (s, 2H), 4.23 (m, 4H), 4.08 (d, 7.2, 1H), 3.79 (m, 1H), 3.61 (d, 10.4, 1H), 3.45 (t, 7.2, 2H), 3.25 (d, 7.3, 1H), 3.18 (m, 5H), 3.07 (m, 1H), 2.93 (s, 9H), 2.09 (m, 1H), 2.41 (m, 2H), 2.33 (m, 1H), 2.27 (s, 3H), 2.24 (m, 2H), 2.10 (s, 3H), 2.02 (m, 4H), 1.94 (s, 3H), 1.86 (m, 1H), 1.80 (s, 3H), 1.69 (m, 1H), 1.60 (m, 2H), 1.54 (m, 3H), 1.27 (m, 2H), 1.22 (m, 1H), 0.92 (m, 9H), 0.81 (d, 6.6, 3H), 0.79 (m, 1H), 0.02 (d, 6.8, 3H), −0.40 (d, 6.6, 3H). $^{13}$C NMR (600 MHz, CD$_2$Cl$_2$:d4-MeOH 9:1, 4 deg C.) δ 193.9, 183.2, 175.3, 174.7, 173.1, 172.0, 171.9, 171.8, 169.8, 161.2, 158.0, 156.1, 147.0, 145.4, 143.9, 141.6, 140.1, 134.6, 134.1, 133.6, 132.4, 132.0, 126.5, 121.7, 120.7, 119.3, 118.9, 112.5, 112.1, 110.6, 108.8, 108.1, 96.0, 91.5, 77.0, 76.8, 74.7, 74.1, 71.2, 65.9, 59.8, 57.0, 47.4, 46.6, 46.5, 40.3, 38.2, 38.0, 37.4, 36.2, 33.3, 31.0, 29.4, 28.8, 26.9, 26.1, 25.7, 22.5, 21.1, 20.5, 19.5, 18.6, 18.5, 10.6, 9.4, 8.3, 7.8.

Example 7 Conjugation of Linker-Antibiotic VI and Antibody in the Preparation of an Anti-WTA Antibody-Antibiotic Conjugate Construction and production of the cysteine-engineered (THIOMAB™, Genentech) variant of an anti-WTA antibody was done as reported previously for other antibodies (WO 2014/194247, incorporated by reference; Junutula, et al., 2008b Nature Biotech., 26(8):925-932). Briefly, a cysteine residue was engineered at the Ala 118 position of the anti-WTA heavy chain to produce its cys 118 THIOMAB™ variant (HC A118C). An anti-WTA antibody-antibiotic conjugate was prepared by conjugating the cysteine-engineered, anti-WTA antibody to the linker-antibiotic VI intermediate. Prior to conjugation, cysteine-engineered, anti-WTA antibodies were partially reduced with TCEP using standard methods in accordance with the methodology described in WO 2004/010957, the teachings of which are incorporated by reference for this purpose. The partially reduced antibodies were conjugated to linker-antibiotic VI intermediate using standard methods in accordance with the methodology described, e.g., in Doronina et al. (2003) *Nat. Biotechnol.* 21:778-784 and US 2005/0238649. Briefly, the partially reduced antibody was combined with VI to allow conjugation of the linker-antibiotic intermediate to reduced cysteine residues of the antibody.

The conjugation reaction was quenched, and the AAC was purified. The antibiotic load (average number of antibiotic moieties per antibody) for each AAC was determined and was between about 1 to about 2 for the anti-wall teichoic acid antibodies engineered with a single cysteine mutant site.

Reduction/Oxidation of ThioMabs for Conjugation:

Full length, cysteine engineered monoclonal antibodies (ThioMabs—Junutula, et al., 2008b Nature Biotech., 26(8): 925-932; Dornan et al (2009) Blood 114(13):2721-2729; U.S. Pat. Nos. 7,521,541; 7,723,485; WO2009/052249, Shen et al (2012) Nature Biotech., 30(2):184-191; Junutula et al (2008) Jour of Immun. Methods 332:41-52) expressed in CHO cells were reduced with about a 20-40 fold excess of TCEP (tris(2-carboxyethyl)phosphine hydrochloride or DTT (dithiothreitol) in 50 mM Tris pH 7.5 with 2 mM EDTA for 3 hrs at 37° C. or overnight at room temperature. (Getz et al (1999) *Anal. Biochem.* Vol 273:73-80; Soltec Ventures, Beverly, Mass.). The reduced ThioMab was diluted and loaded onto a HiTrap S column in 10 mM sodium acetate, pH 5, and eluted with PBS containing 0.3M sodium chloride. Alternatively, the antibody was acidified by addition of 1/20$^{th}$ volume of 10% acetic acid, diluted with 10 mM succinate pH 5, loaded onto the column and then washed with 10 column volumes of succinate buffer. The column was eluted with 50 mM Tris pH7.5, 2 mM EDTA.

The eluted reduced ThioMab was treated with 15 fold molar excess of DHAA (dehydroascorbic acid) or 200 nM aqueous copper sulfate (CuSO$_4$). Oxidation of the interchain disulfide bonds was complete in about three hours or more. Ambient air oxidation was also effective. The re-oxidized antibody was dialyzed into 20 mM sodium succinate pH 5, 150 mM NaCl, 2 mM EDTA and stored frozen at −20° C.

Conjugation of Thio-Mab Antibodies with Linker-Antibiotic Intermediates VI:

The deblocked, reoxidized, thio-antibodies (ThioMab) targeting wall teichoic acid (anti-WTA) were reacted with an excess, such as 6-8 fold molar excess, of the linker-antibiotic intermediate VI (from a DMSO stock at a concentration of about 20 mM) in 50 mM Tris, pH 8, in an aqueous mixture until the reaction was complete (16-24 hours) as determined by LC-MS analysis of the reaction mixture. The aqueous mixture of the conjugation reaction may include a solvent selected from propylene glycol, N-methylpyrrolidone (NMP), dimethylformamide (DMF), dimethylacetamide (DMA), and dimethylsulfoxide (DMSO).

The crude antibody-antibiotic conjugates (AAC) were then applied to a cation exchange column after dilution with 20 mM sodium succinate, pH 5. The column was washed with at least 10 column volumes of 20 mM sodium succinate, pH 5, and the antibody was eluted with PBS. The AAC were formulated into 20 mM His/acetate, pH 5, with 240 mM sucrose using gel filtration columns. AAC were characterized by UV spectroscopy to determine protein concentration, analytical SEC (size-exclusion chromatography) for aggregation analysis and LC-MS before and after treatment with Lysine C endopeptidase.

Size exclusion chromatography was performed using a Shodex KW802.5 column in 0.2M potassium phosphate pH 6.2 with 0.25 mM potassium chloride and 15% IPA at a flow rate of 0.75 ml/min. Aggregation state of AAC was determined by integration of eluted peak area absorbance at 280 nm.

LC-MS analysis was performed using an Agilent QTOF 6520 ESI instrument. As an example, an AAC generated using this chemistry was treated with 1:500 w/w Endoproteinase Lys C (Promega) in Tris, pH 7.5, for 30 min at 37° C. The resulting cleavage fragments were loaded onto a 1000A, 8 um PLRP-S column heated to 80° C. and eluted with a gradient of 30% B to 40% B in 5 minutes. Mobile phase A: H$_2$O with 0.05% TFA. Mobile phase B: acetonitrile with 0.04% TFA. Flow rate: 0.5 ml/min. Protein elution was monitored by UV absorbance detection at 280 nm prior to electrospray ionization and MS analysis. Chromatographic resolution of the unconjugated Fc fragment, residual unconjugated Fab and antibiotic-Fab was usually achieved. The obtained m/z spectra were deconvoluted using Mass Hunter™ software (Agilent Technologies) to calculate the mass of the antibody fragments.

Although the foregoing invention has been described in some detail by way of illustration and example for purposes of clarity of understanding, the descriptions and examples should not be construed as limiting the scope of the invention. Accordingly, all suitable modifications and equivalents may be considered to fall within the scope of the invention as defined by the claims that follow. The disclosures of all patent and scientific literature cited herein are expressly incorporated in their entirety by reference.

What is claimed is:

1. A process for the preparation of benzoxazinorifamycin analog IV,

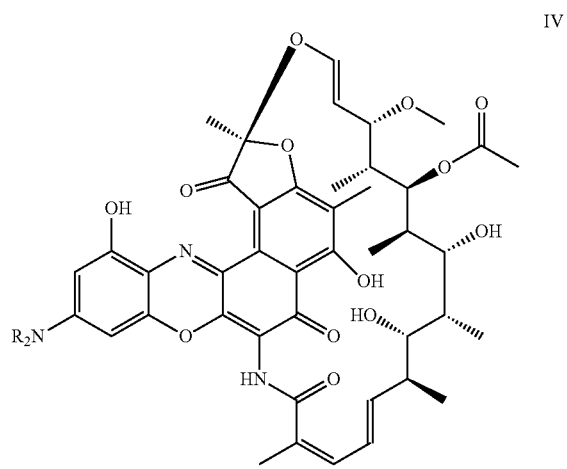

comprising reacting F-benzoxazinorifamycin I,

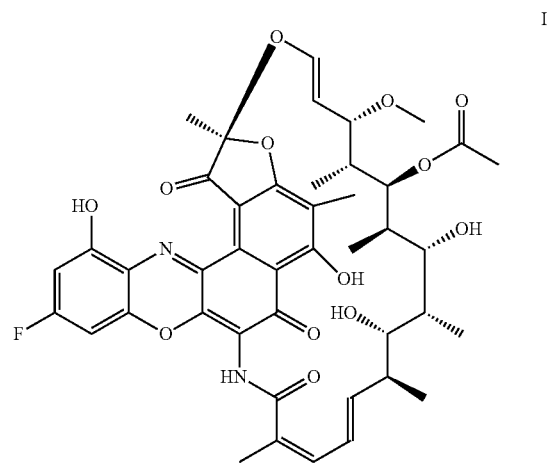 [SMILES: CO[C@H]1/C=C/O[C@@]2(C)Oc3c(C)c(O)c4c(=O)c(c5oc6cc(F)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

and a secondary amine R$_2$NH selected from dimethylamine, diethylamine, di-n-propylamine, 1-methylpiperazine, N1-isobutylpiperazine, and N,N-dimethylpiperidin-4-amine, to form IV, where R is selected from methyl, ethyl, and n-propyl, and where two R groups form 1-methylpiperazine, N1-isobutylpiperazine, and N,N-dimethylpiperidin-4-amine;

wherein F-benzoxazinorifamycin I is prepared by a process comprising:

(i) reacting rifamycin S II, and 2-amino-5-fluorobenzene-1,3-diol III in a batch reactor vessel to form I wherein RIFA SV is formed as a by-product and delivered to a flow-reactor (ii) one or more oxidants oxidizes the RIFA SV to form II in the flow-reactor, wherein the one or more oxidants are selected from 2,2,6,6-tetramethyl-1-piperidinyloxy (TEMPO), oxygen gas comprising about 5% to about 100% of the reaction gas phase, and benzoquinone, and (iii) the II formed in the flow-reactor is delivered to the batch reactor vessel, wherein the one or more oxidants and 2-amino-5-fluorobenzene-1,3-diol III are kept separate.

2. The process of claim 1 wherein the secondary amine is N,N-dimethylpiperidin-4-amine and IV has the structure IVa:

3. The process of claim 1 wherein the secondary amine is N1-isobutylpiperazine and IV has the structure IVb:

4. The process of claim 1 wherein the one or more oxidants is selected from 2,2,6,6-tetramethyl-1-piperidinyloxy (TEMPO) and oxygen gas.

5. The process of claim 1 wherein the one or more oxidants is 2,2,6,6-tetramethyl-1-piperidinyloxy (TEMPO).

6. The semi process of claim 1 wherein the one or more oxidants is benzoquinone.

7. The process of claim 1 wherein rifamycin S II, and 2-amino-5-fluorobenzene-1,3-diol III are dissolved in isopropyl acetate (iPrOAc) in the batch reactor vessel.

8. The process of claim 1 wherein the one or more oxidants is dissolved in isopropyl acetate (iPrOAc) in the flow-reactor.

* * * * *

UNITED STATES PATENT AND TRADEMARK OFFICE
CERTIFICATE OF CORRECTION

PATENT NO. : 10,689,325 B2  
APPLICATION NO. : 16/415612  
DATED : June 23, 2020  
INVENTOR(S) : Stephan Bachmann et al.

Page 1 of 2

It is certified that error appears in the above-identified patent and that said Letters Patent is hereby corrected as shown below:

In the Claims

Column 29, Lines 33-48, Claim 1, please delete the following compound:

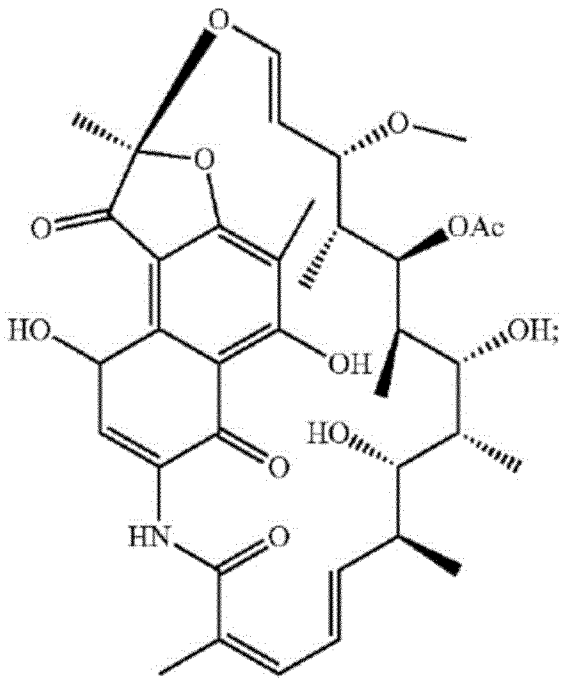

" and insert

Signed and Sealed this  
Twentieth Day of October, 2020

Andrei Iancu  
*Director of the United States Patent and Trademark Office*

CERTIFICATE OF CORRECTION (continued)
U.S. Pat. No. 10,689,325 B2

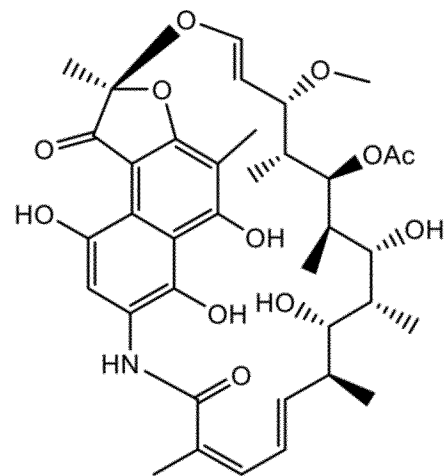

-- ; -- therefor.